(12) United States Patent
Lo et al.

(10) Patent No.: US 7,045,536 B2
(45) Date of Patent: May 16, 2006

(54) COMPOUND HAVING ANTI-VIRAL ACTIVITY

(75) Inventors: Li Ching Lo, Miaoli Couty (TW); Wen Yueh Ho, Taichung (TW); Lien Tai Chen, Taoyuan (TW)

(73) Assignee: Industrial Technology Research Institute, Chutung, Hsinchu (TW)

( * ) Notice: Subject to any disclaimer, the term of this patent is extended or adjusted under 35 U.S.C. 154(b) by 118 days.

(21) Appl. No.: 10/677,218

(22) Filed: Oct. 3, 2003

(65) Prior Publication Data

US 2004/0254147 A1    Dec. 16, 2004

(30) Foreign Application Priority Data

Jun. 13, 2003    (TW) .............................. 92116094 A

(51) Int. Cl.
*A61K 31/415*    (2006.01)
*A61K 31/47*    (2006.01)

(52) U.S. Cl. ...................... 514/332; 514/397; 546/255; 548/335.1

(58) Field of Classification Search ................ 514/332, 514/397; 546/255; 548/335.1
See application file for complete search history.

(56) References Cited

FOREIGN PATENT DOCUMENTS

DE    2708331 A1 *  9/1977

OTHER PUBLICATIONS

Jeong et al, Tetrahedron Letters, vol. 38, No. 18, pp. 3279-3282, 1997.*

* cited by examiner

*Primary Examiner*—Zinna N. Davis
(74) *Attorney, Agent, or Firm*—Bacon & Thomas, PLLC

(57) ABSTRACT

The present invention discloses an organic ionic compound having anti-viral activity and the method for antagonizing virus in vitro by putting the compounds in contact with the virus.

3 Claims, 2 Drawing Sheets

Concentration of py-C3-py (mg/ml)

Concentration of Im-C3-Im (mg/ml)

COMPOUND HAVING ANTI-VIRAL ACTIVITY

BACKGROUND OF THE INVENTION (A) Field of the Invention

The present invention relates to an organic ionic compound having anti-viral activity and the method for antagonizing virus in vitro by putting the compound in contact with the virus.

(B) Description of Related Art

Virus may be spread through air, secretions from nose or mouth, or from direct contact and cause diseases. Enterovirus infection that is active in the summer and autumn seasons in Taiwan poses a significant threat to the health of the general population, in particular children. Enterovirus may be transmitted by contacting the oral or nasal secretions (e.g. saliva, sputum and nasal mucus) or feces of the patient. Hence it is easy to cause epidemics in crowded areas. Current approach to the management of enterovirus infection is supportive treatment. In light that enterovirus exists in many types and has variability, people who are previously exposed to one type of enterovirus are not immune to other types of enterovirus. The precautions against viral infection are no other than washing hands constantly, keeping the home environment clean and well-ventilated, wearing masks and avoiding direct contact with patients.

Organic ionic compounds are used mainly in conducting material, electrolyte, catalyst, surfactant, and new types of solvent (Sheldon R., Chem. Commun. 2399–2407 (2001)). So far, no patent or literature has been disclosing the anti-viral effect of organic ionic compounds. The present invention is the first to propose the application of such compounds to antagonizing virus activity.

SUMMARY OF THE INVENTION

The main objective of the present invention is to provide an anti-viral compound having the general formula (I):

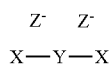
(I)

wherein

X represents a heterocyclic cation, comprising at least one hetero atom selected from a group consisting of free nitrogen, sulfur and oxygen, where the nitrogen on the heterocyclic ring may be optionally substituted with $C_1$–$C_4$ alkyl. The actual examples of X include but are not limited to pyridinium, pyridazinium, pyrimidinium, pyrazinium, imidazolium, N—($C_1$–$C_4$ alkyl) substituted imidazolium, pyrazolium, N—($C_1$–$C_4$ alkyl) substituted pyrazolium, thiazolium, pyrrolidinium or oxazolium, and preferably pyridinium or imidazolium;

Y is —$(CH_2)_n$—;

n is an integer ranging from 2 to 9, and preferably 3; and $Z^-$ is halide ion (e.g. fluoride ion, chloride ion, bromide ion, and iodide ion), hexafluorophosphorate or tetrafluoroborate, and preferably bromide ion.

Another objective of the present invention is to provide an anti-viral composition comprising a compound having the general formula (I):

wherein X, Y and $Z^-$ are defined the same as above, and its acceptable carrier, diluent or excipient.

Further provided by the present invention is a method for antagonizing virus in vitro by putting the organic ionic compound disclosed in this invention in contact with the virus to inhibit its activity.

Still further provided by the present invention is a method for antagonizing virus in vitro by putting the composition containing the organic ionic compound disclosed in this invention in contact with the virus to inhibit its activity.

DETAILED DESCRIPTION OF THE INVENTION

Figure 1A:
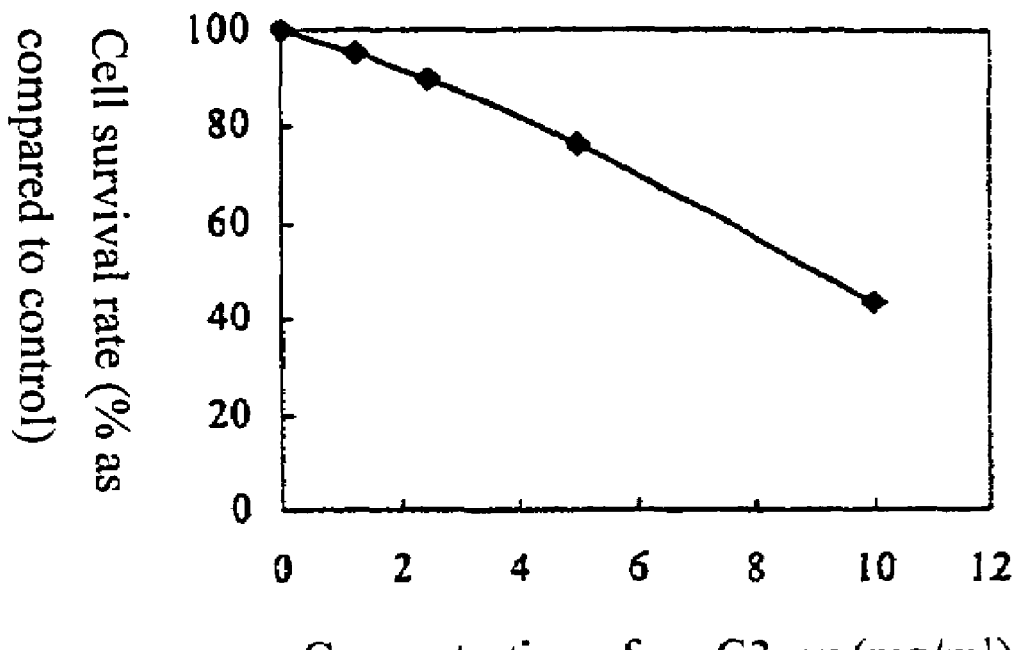
FIG. 1A shows the toxicity ($LC_{50}$) of ionic solution dibromo1,1'-glyceryl-bispyridine of the present invention to RD cells.

The organic ionic compound of the present invention is constituted entirely of positively-charged ions and negatively-charged ions. The compound possesses the properties of high boiling point, high charge density, and thermal stability (Wikes J. S. and Zaworotko M. 'J. Chem. Commun. 965–967 (1992)). It differs from typical organic solvent in which such organic ionic compound does not vaporize under room temperature, hence does not release harmful gases into the air in the process of experiments. Its use is convenient and it may be recycled for repeated use, which helps reduce the generation of waste and hence is environmentally friendly (Rebecca Renner 'Scientific American' August 2001).

The commonly seen cations in organic ionic compounds are quaternary ammonium, imidazolium, and pyridinium; and the commonly seen anions include $BF_4^-$, $PF_6^-$, $OTf^-$ ($CF_3SO_3^-$), $NTf_2^-$ ($N(CF_3S$ $CTf_3^-$ ($C(CF_3SO_2)_3^-$), $CF_3COO^-$, $C_3F_7COO^-$, $C_4F_9SO_3^-$, $N(C_2F_5SO_2)_2^-$, $PO_4^-$, and $NO_3^-$ (Li R. and Wang J., Chem. J. Internet 4 (4): 16(2002)). As described earlier, currently organic ionic compounds are used primarily in conducting material, battery electrolyte, catalyst and environmentally friendly solvent. So far, no products containing organic ionic compounds claim anti-viral activity.

The main objective of the present invention is to provide a compound having anti-viral activity and the general formula (I):

(I)

wherein

X represents a heterocyclic cation, comprising at least one hetero atom selected from a group consisting of free nitrogen, sulfur and oxygen, where the nitrogen on the heterocyclic ring may be optionally substituted with $C_1$–$C_4$ alkyl. The actual examples of X include but are not limited to pyridinium, pyridazinium, pyrimidinium, pyrazinium, imidazolium, N—($C_1$–$C_4$ alkyl) substituted imidazolium, pyrazolium, N—($C_1$–$C_4$ alkyl) substituted pyrazolium, thiazolium, pyrrolidinium or oxazolium, and preferably pyridinium or imidazolium;

Y is —$(CH_2)_n$—;

n is an integer ranging from 2 to 9, and preferably 3; and $Z^-$ is halide ion (e.g. fluoride ion, chloride ion, bromide ion, and iodide ion), hexafluorophosphate or tetrafluoroborate, and preferably bromide ion.

Another objective of the present invention is to provide an anti-viral composition comprising a compound having the general formula (I):

(I)

wherein X, Y and $Z^-$ are defined the same as above, and its acceptable carrier, diluent or excipient.

The term "$C_1$–$C_4$ alkyl" in the definition of general formula (I) refers to methyl, ethyl, propyl, isopropyl, n-butyl, isobutyl, secondary butyl or tertiary butyl.

In a preferred embodiment of the present invention, the anti-viral compound has general formula (I):

(I)

wherein X is pyridinium or imidazolium, Y is —$(CH_2)_3$—, and $Z^-$ is bromide ion; and its acceptable carrier, diluent or excipient.

Further provided by the present invention is a method for antagonizing virus in vitro by putting the organic ionic compound of this invention having the general formula (I) in contact with the virus to inhibit the virus activity:

(I)

wherein X, Y and $Z^-$ are defined the same as above.

Still further provided by the present invention is a method for antagonizing virus in vitro by putting a composition containing the organic ionic compound of this invention in contact with the virus to inhibit the virus activity.

The term "virus" depicted in the prevent invention refers to in particular viruses in the small RNA virus family (Picornaviridae), preferably Enterovirus, and more preferably enterovirus type 71.

The organic ionic compound of the present invention may be used as is, or preferably with carrier, diluent, excipient or adjuvant prepared using conventional techniques. For this purpose, the organic ionic compound of the present invention may be added with suitable excipient using known techniques to turn into emulsified concentrate (e.g. hand-washing lotion, detergent, laundry detergent and shampoo), coatable pastel (e.g. coating material), sprayable solution (e.g. spray), diluted solution (e.g. beverage and health food product), filler (e.g. used in toys and wipe cloth), powder miscible with carrier, dissolvable powder, particles, and granules, or enveloped in suitable coating agent (e.g. used in air filter, water filter, mask, and filter membrane). In the form of composition, the organic ionic compound of the prevent invention may, depending on the purpose and application environment, be applied in the form of spray, mist, coating or emulsion. The composition may also contain other adjuvant, such as stabilizer, foam buster, viscosity adjuster, binder, viscosity increasing agent or other formulations that produce special effect.

The organic ionic compound of the present invention is typically used in the form of composition, or simultaneously or consecutively used with other compounds. For example, it may be used with other anti-viral drugs or their mixtures or nutritional ingredients to enhance the synergistic anti-viral effect.

If necessary, the organic ionic compound of the present invention may be formulated into a medical composition for fighting virus (preferably infections caused by Enterovirus and more preferably by enterovirus type 71) that can treat or prevent enterovirus infection or serious enterovirus infection. The organic ionic compound may be used alone or combined with medically acceptable carrier or excipient and dispensed in single dose or multiple doses. Medically acceptable carrier or diluent and any other known adjuvant and excipient may be prepared according to conventional techniques as provided, for example, in Remington's Pharmaceutical Sciences, Edition 19, Edited by Gennaro, Mack Publishing, Easton, Pa. (1995).

The medical composition provided herein may be specifically formulated for suitable route of administration, e.g. oral, rectal, nasal, pulmonary, local (including buccal and sublingual), percutaneous, intracisternal, intraperitoneal, vaginal and parenteral (including subcutaneous, intramuscular, intraspinal, intravenous and intracutaneous). It should be noted that the preferred route of administration is determined by the general symptoms, age of the patient, characteristics of the target symptoms, and the active ingredient selected.

The medical composition given orally may be in solid form, such as capsule, tablet, sugar-coated tablet, pill, powder and granule, which may be suitably prepared by known techniques with film (e.g. enteric-coated) or prepared in such a way that the release of its active ingredients is under control, such as in sustained or extended release.

The medical composition may be in liquid form to be given orally, such as solution, emulsion, suspension, syrup, and elixir, or given parenterally, such as sterile aqueous and non-aqueous injection solution, aqueous dispersion, suspension or emulsion, and sterile powder to be dissolved before use in sterile injection solution or aqueous dispersion.

Other suitable forms of the medical composition herein include suppository, spray, ointment, cream, gel, inhalant, skin patch, and implant.

The actual dosage of the medical composition containing organic ionic compound of the present invention shall be decided by the frequency and mode of administration, patient's gender, age, weight and general conditions, characteristics of target symptoms, severity, and accompanying illness.

BRIEF DESCRIPTION OF THE PREFERRED EMBODIMENTS

The preparation and efficacy of organic ionic compound in the present invention are further depicted with the illustration of embodiments, which however are not meant to limit the scope of the present invention.

Embodiment 1

Preparation of dibromo 1,1'-glyceryl-bis (3-methyl-1H-imidazole)

In this embodiment, 2.05 gram (25 mol) of 1-methyl imidazole is added into methanol (10 ml) solution containing 2.02 gram (10 mmol) of 1,3-dibromo propane under room temperature. The reaction mixture is heated to 75° C. and subject to 40 hours of reflux agitation to achieve complete reaction. The mixture is then cooled down to room temperature and rinsed with 100 ml ethyl acetate twice. After vacuum dry, the target product is obtained with yield of 89%.

$^1$H NMR (D$_2$O): 8.8, 7.6–7.5, 4.3–4.2, 3.9, 2.7–2.5 ppm.

Embodiment 2

Preparation of dibromo 1,1'-glyceryl-bispyridine

In this embodiment, 1.98 gram (25 mol) of pyridine is added into methanol (10 ml) solution containing 2.02 gram (10 mmol) 1,3-dibromo propane under room temperature. The reaction mixture is heated to 75° C. and subject to 40 hours of reflux agitation to achieve complete reaction. The mixture is then cooled down to room temperature and rinsed with 100 ml ethyl acetate twice. After vacuum dry, the target product is obtained with yield of 82%.

1H NMR (D2O): 9.0–8.9, 8.7–8.6, 8.2–8.1, 4.9–4.8, 3.6–3.5, 2.7–2.6 ppm.

Embodiment 3

Cell Culturing

In this embodiment, rhabdomyosarcoma (RD) cells obtained from the Virology Lab of Chang Gung Memorial Hospital are cultured in DMEM (Gibco) containing 10% fetal bovine serum and placed in 5% CO$_2$, 37° C. incubator. In successive culture, the cells are rinsed twice with 1× PBS and then added with proper amount of 0.25% trypsin-EDTA (Gibco) for cell treatment. After the cells drop off from the surface of culture dish, add DMBM medium containing 10% fetal bovine serum to disperse the cells evenly in the culture dishes. Place the dishes into 5% CO$_2$, 37° C. incubator to continue the culturing.

Embodiment 4

Virus Culturing

In this embodiment, enterovirus 71/Tw/2231/98 obtained from Virology Lab of Chang Gung Memorial Hospital is diluted with fetal bovine serum free culture medium. Culture the RD cells in DMEM containing 10% fetal bovine serum. When the cells are 90% cultured, wash with 1×PBC once and add the aforesaid diluted virus fluid into the culture medium. Place the medium in the 5% CO$_2$, 35° C. incubator for inoculation for one hour and then add DMEM containing 2% fetal bovine serum. Place the medium in 5% CO$_2$, 35° C. incubator. When over 95% of the cells become round and drop off, collect the supernatant. After centrifuge, freezing and thawing, refrigerate the virus supernatant under −80° C.

Embodiment 5

Toxicity Test

In this embodiment, cultured cells from Embodiment 3 are cultured in 96-well plate. After the cells are mixed with the tested compound for one hour, add DMEM containing 2% fetal bovine serum, and place the medium in 5% CO2, 35° C. incubator for 3–4 days. To read the test result, add 5% formalin to fixate for 1–2 hours and dye with 0.1% crystal violet (J. T. Baker) for 2–3 minutes. Rinse with water and measure $OD_{570nm}$ values.

Embodiment 6

Neutralization Test

In this embodiment, cultured cells from Embodiment 3 are cultured in 96-well plate. After mixing fixed-quantity of virus fluid with the tested compound, add in culture medium for inoculation for one hour, and then add in DMEM containing 2% fetal bovine serum. Place the medium in 5% CO2, 35° C. incubator for 3–4 days. To read the test result, add 5% formalin to fixate for 1–2 hours and dye with 0.1% crystal violet for 2–3 minutes. Rinse with water and measure $OD_{570nm}$ values.

Figure 1B:
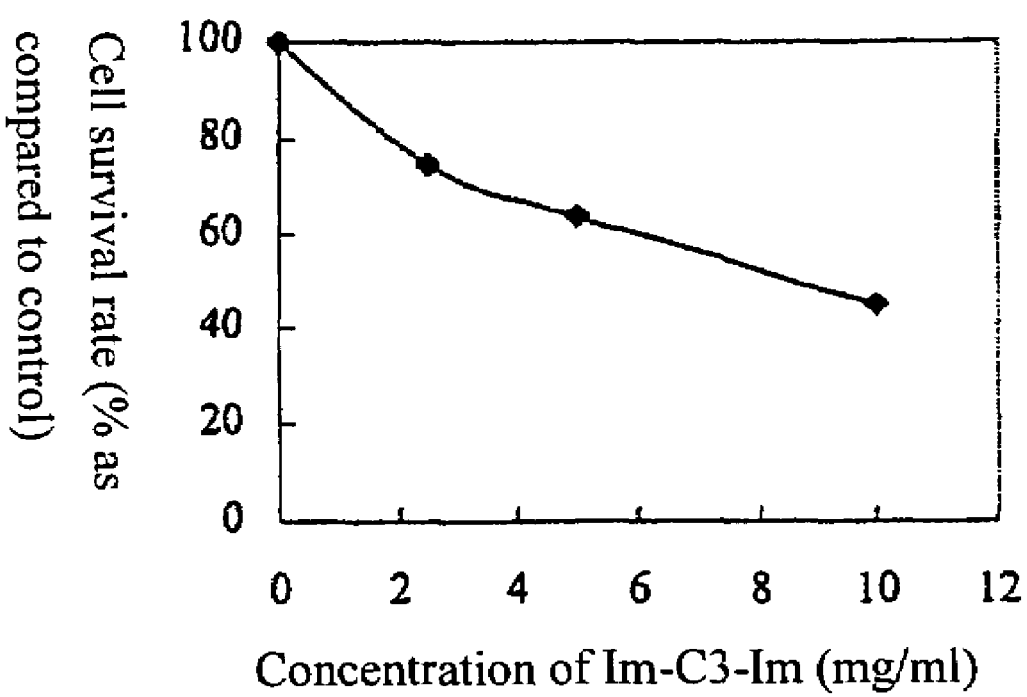
FIG. 1B shows the toxicity ($LC_{50}$) of ionic solution dibromo1,1'-bis (3-methyl-1H-imidazole) of the present invention to RD cells.
Figure 2:
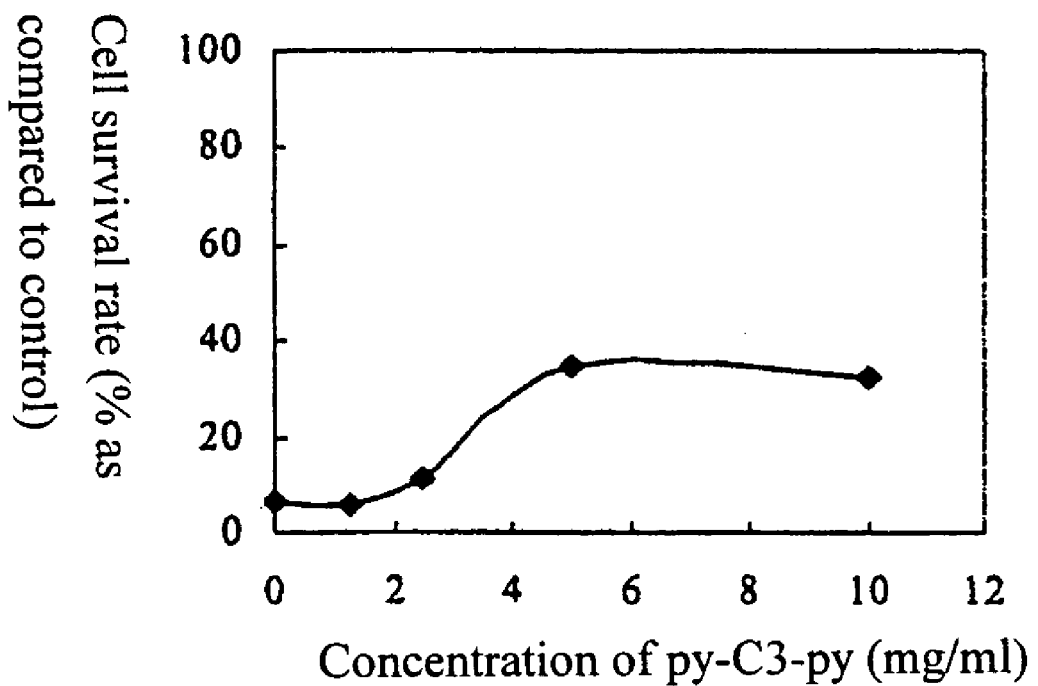
FIG. 2A shows the effect of ionic solution dibromo1,1'-glyceryl-bispyridine of the present invention on inhibiting the activity of enterovirus type 71.
FIG. 2B shows the effect of ionic solution dibromo 1,1'-bis (3-methyl-1H-imidazole) of the present invention on inhibiting the activity of enterovirus type 71.
Figure 2:
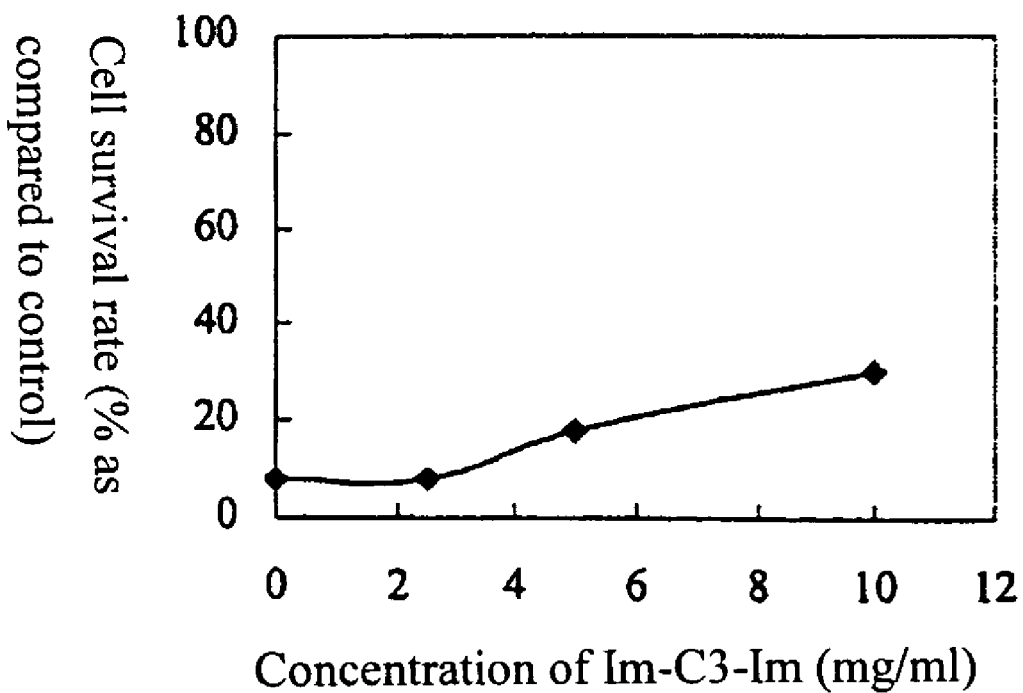

As shown in FIG. 1 and FIG. 2, in the neutralization test, the tested compounds—dibromo 1,1'-glyceryl-bispyridine and dibromo 1,1'-glyceryl-bis (3-methyl-1H-imidazole) at the concentration of 10 mg/ml show 30% and 32% inhibitory effect on enterovirus type 71 respectively. In comparison with other compounds (data not shown), the ionic solution of the present invention has marked anti-viral activity. In the toxicity test, the $LC_{50}$ of 1,1'-glyceryl-bispyridine and dibromo 1,1'-glyceryl-bis (3-methyl-1H-imidazole) are respectively 9.2 mg/ml and 8.4 mg/ml, suggesting higher drug tolerance than other compounds.

As shown in the embodiments described above, the organic ionic compound of the present invention is effective against enterovirus, in particular enterovirus type 71. Thus such compounds may be used in, for example, air filter, filter membrane, mask, handwashing lotion, water filter, coating material and wipe cloth that can adsorb and trap the virus to minimize human contact with the virus. On the other hand, material having anti-viral activity can deactivate the virus on it and render the virus non-infectious, which aids the prevention against the spread of virus. Thus the present invention offers considerable value in industrial applications.

The organic ionic compound of the present invention has been disclosed in the embodiments. However the embodiments should not be construed as a limitation on the actual applicable scope of the invention, and as such, all modifications and alterations without departing from the spirits of the invention and appended claims shall remain within the protected scope and claims of the invention.

What is claimed is:

1. A method for antagonizing enterovirus in vitro by putting compound of general formula (I) in contact with an enterovirus to inhibit the activity of the enterovirus:

(I)

$$\begin{array}{ccc} & Z^- \quad Z^- & \\ X & — Y — & X \end{array}$$

wherein

X is pyridinium or imidazolium;

Y is $-(CH_2)_n-$;

n is an integer ranging from 2 to 9; and $Z^-$ is hexafluorophosphorate.

2. The method according to claim 1, wherein Y is $-(CH_2)_3-$.

3. The method according to claim 1, wherein the enterovirus is enterovirus type 71.

* * * * *